US00PP26436P2

(12) United States Plant Patent
Pounders et al.

(10) Patent No.: US PP26,436 P2
(45) Date of Patent: Mar. 1, 2016

(54) AZALEA PLANT NAMED 'AZ 16'

(50) Latin Name: *Rhododendron hybrida*
Varietal Denomination: AZ 16

(71) Applicants: The United States of America, as represented by the Secretary of Agriculture, Washington, DC (US); Capstone Plants Inc., Grand Saline, TX (US)

(72) Inventors: Cecil T Pounders, Poplarville, MS (US); James B Berry, Mineola, TX (US)

(73) Assignees: CAPSTONE PLANTS, INC., Grand Saline, TX (US), part interest; THE UNITED STATES OF AMERICA, AS REPRESENTED BY THE SECRETARY OF AGRICULTURE, Washington, DC (US), part interest ( * ) Notice: Subject to any disclaimer, the term of this patent is extended or adjusted under 35 U.S.C. 154(b) by 134 days.

(21) Appl. No.: 13/998,697

(22) Filed: Nov. 25, 2013

(51) Int. Cl.
*A01H 5/02* (2006.01)

(52) U.S. Cl.
USPC ..... Plt./240

(58) Field of Classification Search
USPC ..... Plt./240
See application file for complete search history.

*Primary Examiner* — Keith Robinson
(74) *Attorney, Agent, or Firm* — Penny J. Aguirre

(57) ABSTRACT

A new cultivar of Azalea named 'AZ 16' that is characterized by its uniform flower color and size, its strong flowering during its extended flowering season blooming in late March to early April and then again in late August through October in Mississippi, its large pink flowers with red flecks and red undertones on the upper surface of the petals, its leaves that retain a burgundy color through winter and into the spring bloom season, its rapid development and a tight crown with only minimum pruning required when grown under optimum conditions in containers, and its exceptional environmental stress tolerance including fluctuations in moisture and temperature stress, and its good disease and pest resistance.

2 Drawing Sheets

Botanical classification: *Rhododendron hybrida.*
Cultivar designation: 'AZ 16'.

BACKGROUND OF THE INVENTION

The present invention relates to a new and distinct cultivar of *Rhododendron* plant of hybrid origin, botanically known as *Rhododendron hybrida* 'AZ 16' and will be referred to hereafter by its cultivar name, 'AZ 16'. 'AZ 16' is a new cultivar of evergreen Azalea grown for use as a landscape plant.

The new cultivar was developed through an on-going breeding program conducted by the Inventors in Poplarville, Miss., USA. The objectives of the breeding program are to develop new cultivars of Azalea that exhibit tolerance to environmental stresses and disease resistance combined with unique flower colors and extended bloom periods.

The new cultivar arose from a cross made in spring of 2005 in Poplarville, Miss. between 'Red Slippers' (not patented) as the female parent and 'Fourth of July' (not patented) as the male parent. The Inventors selected 'AZ 16' as a single unique plant amongst the seedlings that resulted from the above cross in fall of 2007.

Asexual propagation of the new cultivar was first accomplished by softwood stem cuttings in Poplarville, Miss. in spring of 2008 by one of the Inventors. Asexual propagation by softwood and semi-hardwood stem cuttings has determined that the characteristics of the new cultivar are stable and are reproduced true to type in successive generations.

SUMMARY OF THE INVENTION

The following traits have been repeatedly observed and represent the characteristics 'AZ 16'. These attributes in combination distinguish 'AZ 16' as a new and distinct cultivar of Azalea.

1. 'AZ 16' exhibits uniform flower color and size and strong flowering during its extended flowering season blooming in late March to early April and then again in late August through October in Mississippi.
2. 'AZ 16' exhibits large pink flowers with red flecks and red undertones on the upper surface of the petals.
3. 'AZ 16' exhibits large leaves that retain a burgundy color through winter and into the spring bloom season.
4. 'AZ 16' exhibits rapid development and a tight crown with only minimum pruning required when grown under optimum conditions in containers.
5. 'AZ 16' exhibits good environmental stress tolerance including fluctuations in moisture and temperature stress; thriving in summer temperatures that exceed 100° F. for 90 days or more and incurring no stem or flower bud damage when exposed to temperatures down to 14° F.
6. 'AZ 16' has been observed to be disease and insect free (roots and foliage) under the conditions grown with resistance observed to root rot, lace bugs, spider mites, and petal blight.

The female parent of 'AZ 16', 'Red Slippers', differs from 'AZ 16' in having flowers that are reddish pink in color and in having a less compact plant habit. The male parent, of 'AZ 16', 'Fourth of July', differs from 'AZ 16' in having much less cold hardiness. 'AZ 16' can also be most closely compared to the cultivars 'Indian Summer' (not patented), a Gable azalea, and the 'RLH1-1P2' (U.S. Plant Pat. No. 21,562). 'Indian Summer' differs from 'AZ 16' in having a less compact plant habit and less heat tolerance, in having flowers that are yellowed coral pink in color, and in having a less vigorous second bloom season. 'RLH1-1P2' differs from 'AZ 16' in having flowers that are crimson red in color and much greater susceptibility to petal blight (*Ovulinia azaleae* Weiss).

BRIEF DESCRIPTION OF THE DRAWINGS

The accompanying colored photograph illustrates the overall appearance and distinct characteristics of the new Azalea. The photographs were taken of six year-old plants of 'AZ 16' as grown outdoors in a 15-gallon container in Poplarville, Miss.

The photograph in FIG. 1 provides a side view of 'AZ 16' in bloom.

Figure 1:
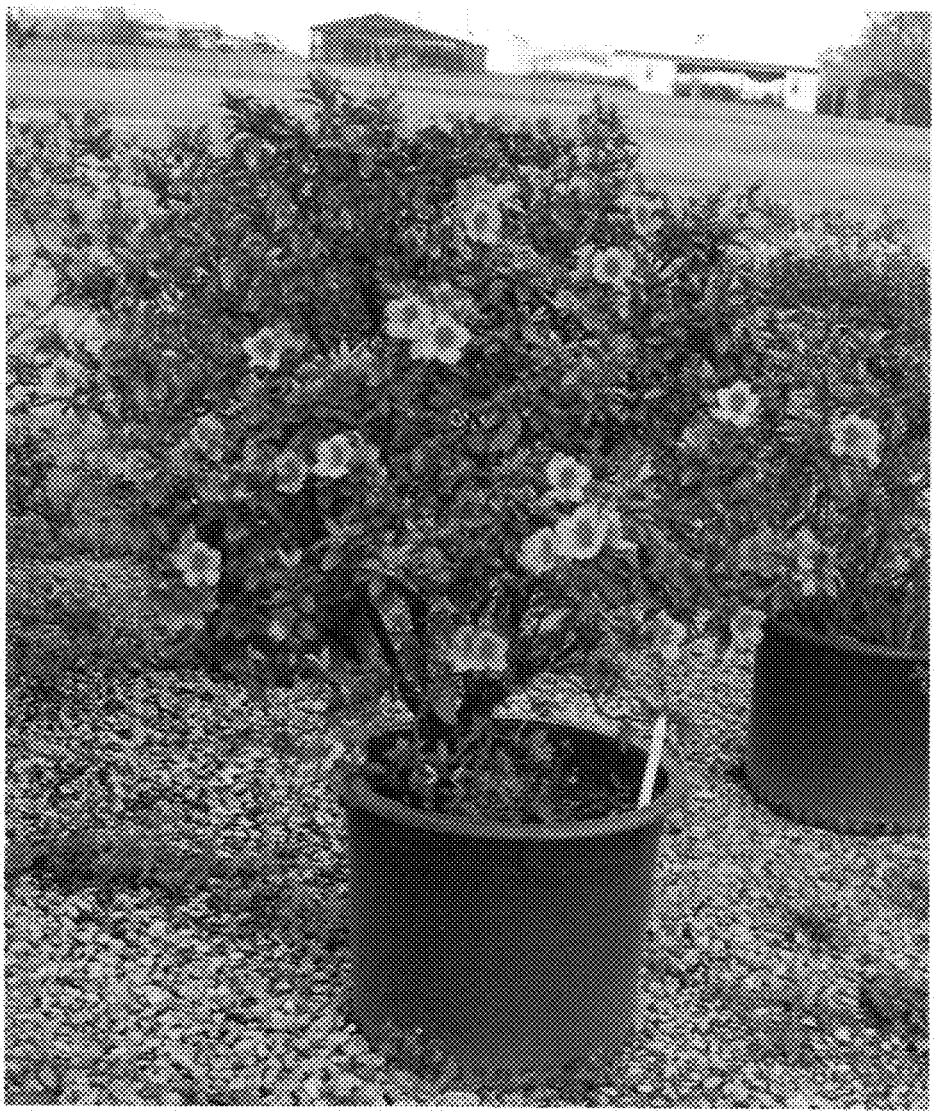
Figure 2:
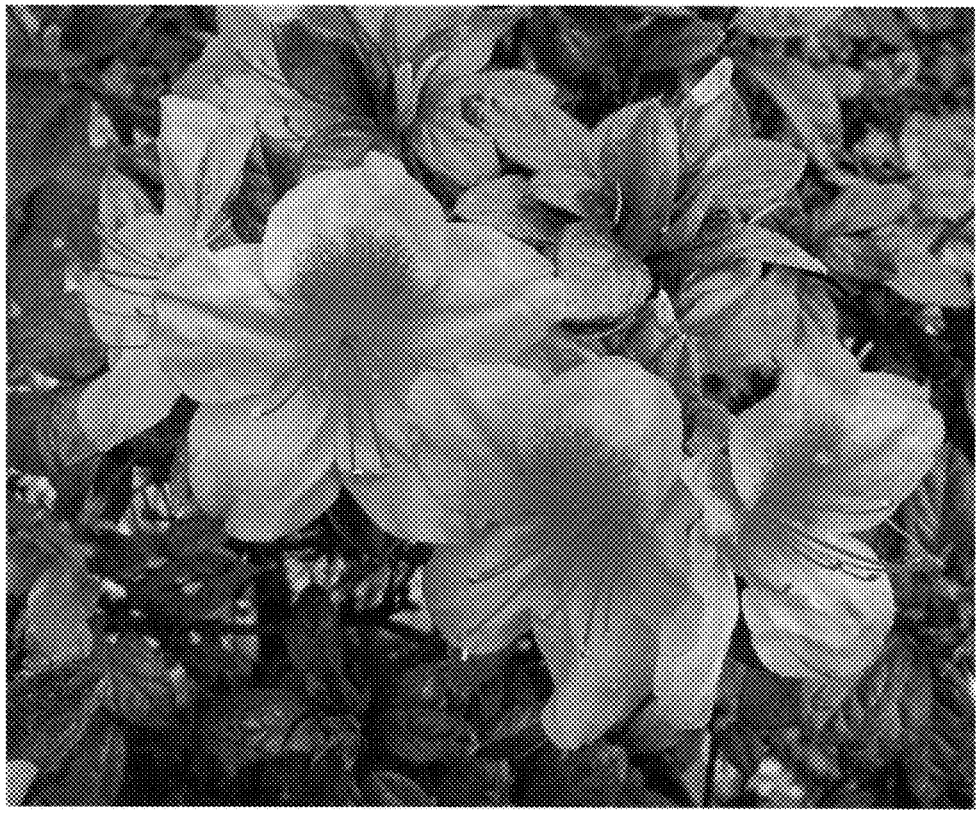

The photograph in FIG. 2 provides a close-up view of the flowers of 'AZ 16'.

The colors in the photographs are as close as possible with the digital photography and printing techniques utilized and the color codes in the detailed botanical description accurately describe the new Azalea.

DETAILED BOTANICAL DESCRIPTION OF THE PLANT

The following is a detailed description of 18 month-old plants of the new cultivar as grown outdoors in three-gallon containers in Grand Salinas, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Late March to early April and late August through October (Until hard freeze) in Poplarville, Miss., USA.

*Plant type*.—Evergreen shrub.

*Plant habit*.—Upright, dense crown, and mounded.

*Height and spread*.—Reaches an average of 1 m in height and 1.5 m in spread in the landscape for 6 years.

*Hardiness*.—At least in U.S.D.A. Zones 7 to 8.

*Environmental stresses*.—Good environmental stress tolerance including fluctuations in moisture and temperature stress; thriving in summer temperatures that exceed 100° F. for 90 days or more and incurring no stem or flower bud damage when exposed to temperatures down to 14° F.

*Diseases and pests*.—Has been observed to be disease and insect free (roots and foliage) under the conditions grown with resistance to root rot (*Phytophthora* spp.), lace bugs (*Stephanitis pyrioides*), spider mites (*Eotetranychus clitus*), and petal blight (*Botrytis cinerea*).

*Root description*.—Abundant, fibrous, moderately dense, and 199D in color.

*Propagation*.—Softwood or semi-hardwood stem cuttings.

*Root development*.—An average of eight weeks for root initiation and about six months to produce a young rooted plant.

*Growth rate*.—Vigorous.

Stem description:

*Shape*.—Round.

*Stem color*.—New growth; 151A with markings and hairs of 175A, mature wood; a blend of 177A and 177B.

*Stem size*.—Main stems; an average of 8 cm in length and 1 cm in width, lateral stems; an average of 30 cm in length and 4 mm in diameter.

*Stem surface*.—New growth; very pubescent, mature wood; ridged bark, exfoliating.

*Stem aspect*.—Held upright at an average angle of 15° (0°=vertical).

*Stem strength*.—Strong.

*Branching*.—Densely-branched, an average of 30 lateral branches in a 3-gallon container, a tight crown is formed with only minimum pruning required when grown under optimum conditions in containers.

*Internode*.—Average of 1 cm in mid-range of lateral branches.

Foliage description:

*Leaf shape*.—Oblanceolate.

*Leaf division*.—Simple.

*Leaf base*.—Cuneate.

*Leaf apex*.—Mucronate.

*Leaf venation*.—Pinnate, upper and lower surface match leaf color; upper and lower surface moderately covered with stiff pubescence; 1 mm in length, upper surface matches vein color, lower surface 179A in color.

*Leaf margins*.—Entire.

*Leaf attachment*.—Petiolate.

*Leaf arrangement*.—Alternate.

*Leaf orientation*.—Held horizontal to upright.

*Leaf aspect*.—Cupped downward.

*Leaf surface*.—Upper and lower surface coriaceous, cartilaginous, and shiny.

*Leaf color*.—Young leaves upper surface; 137A, young leaves lower surface; 146B, mature leaves upper surface; 146A, mature leaves lower surface; 146C and suffused with N79A in winter through spring.

*Leaf size*.—Average of 6 cm in length, and 3 cm in width.

*Leaf quantity*.—About 20 leaves per lateral branch 30 cm in length.

*Petioles*.—Average of 7 mm in length and 3 mm in diameter, 151A in color, sparsely pubescent surface, moderately strong.

Flower description:

*Inflorescence type*.—Flowers are solitary and occasionally in pairs, semi-double (petaloids) to single depending on weather conditions.

*Lastingness of flowers*.—About 10 days, self cleaning.

*Flower size*.—An average of 4.3 cm in depth and 4.5 cm in diameter.

*Flower fragrance*.—None.

*Flower shape*.—Tubular base with flared petal lobes.

*Flower number*.—Average of 3 per lateral stem.

*Flower aspect*.—Outward, held at an average angle of 45° from vertical.

*Flower bud*.—Ovate in shape, an average of 2.6 cm in length and 1.4 cm in width, acute apex, cuneate base, color; a blend of 58B and 60A with sepal portion 144B suffused with 58B, sepal margins are pubescent with hairs an average of 1.5 mm in length and NN155C in color.

*Flower attachment*.—Pedicel.

*Petal number*.—5.

*Petal shape*.—Spatulate with fused base and upper lobe obovate.

*Petal aspect*.—About 20% fused into tube with lobes flared and slightly overlapping.
*Petal color*.—58B to 58D, internal freckles 59C in color.
*Petal surface*.—Both surfaces glabrous.
*Petal margins*.—Entire and slightly wavy.
*Petal apex*.—Rounded and retuse.
*Petal base*.—Fused.
*Petal size*.—Average of 4 cm in length and 2.2 cm in width.
*Petaloids*.—An average of 7, spathulate and distorted in shape and wrapped around stamen filaments, range from 3 to 8 mm in length and up to 1.5 mm in width, color; base is 58D, 157C near apex, undulating margins, rounded apex and narrow acuminate base.
*Sepal number*.—5.
*Sepal shape*.—Oblong.
*Sepal margin*.—Entire.
*Sepal size*.—Up to 7 mm in length and 4 mm in width.
*Sepal aspect*.—Upright.
*Sepal surface*.—Glossy, covered with long strigose pubescence on both surfaces; up to 2 mm idlength and NN155C in color.
*Sepal apex*.—Rounded to acute.
*Sepal base*.—Fused.
*Sepal color*.—Center is 144B suffused with 58B.
*Calyx*.—Campanulate in shape, average of 1 cm in length and 6 mm in diameter.
*Peduncles*.—An average of 1.3 cm in length and 1.5 mm in diameter, 61B in color, blending down towards the base and becoming 145B, surface is glossy and densely covered with long strigose pubescence, up to 2 mm in length and NN155C in color, held at an average angle of 45° from the stem, moderately strong.
*Pedicels*.—None.
*Bracts*.—Average of 3 at base of flower or pair, wedge-shaped and cupped inward and occasionally with leaf-like tip, up to 1.5 cm in length and 8 mm in width, both surfaces are a blend of 146A and 145A to 145C in color, base truncate, apex acute to acuminate, glabrous on both surfaces and moderately covered with strigose pubescence, an average of 1 mm in length and NN155C in color.

Reproductive organs:

*Gynoecium*.—1 Pistil, an average of 3.5 cm in length, stigma; clavate in shape, an average of 1 mm in diameter and a blend of N66A and 52A in color, style; an average of 3 cm in length, 1 mm in width and 52A to 52B in color, ovary; conical in shape, 4 mm in length and 2 mm in width, rounded apex with circular depression on the top, 138A blending into 61B at the tip in color, heavily pubescent with hairs an average of 1 mm in length and NN155C in color.
*Androecium*.—Stamens; average of 6, surrounded by petaloids with the upper 5 mm extending beyond corolla, filament; average of 2.5 cm in length, 52A to 52B in color, anthers; dorsifixed, an average of 3.5 mm in length, a blend of N186A, N199A and N199B in color, no pollen observed.
*Fruit/seeds*.—Seed pod an average of 15 mm in length and 5 mm in width, matures from 139C to 200B in color.

It is claimed:

1. A new and distinct cultivar of Azalea plant named 'AZ 16' as herein illustrated and described.

* * * * *